(12) United States Patent
Elsbury

(10) Patent No.: US 10,172,647 B2
(45) Date of Patent: Jan. 8, 2019

(54) POLY-AXIAL IMPLANT FIXATION SYSTEM

(75) Inventor: Andrew Elsbury, Fortville, IN (US)

(73) Assignee: Nexxt Spine, LLC, Fishers, IN (US)

( * ) Notice: Subject to any disclaimer, the term of this patent is extended or adjusted under 35 U.S.C. 154(b) by 1551 days.

(21) Appl. No.: 12/947,761

(22) Filed: Nov. 16, 2010

(65) Prior Publication Data

US 2011/0160778 A1 Jun. 30, 2011

Related U.S. Application Data

(60) Provisional application No. 61/261,597, filed on Nov. 16, 2009.

(51) Int. Cl.
*A61B 17/70* (2006.01)

(52) U.S. Cl.
CPC .................. *A61B 17/7037* (2013.01)

(58) Field of Classification Search
CPC ............ A61B 17/7037; A61B 17/7062; A61B 17/7035
USPC ........ 606/305–308, 319, 320, 328, 264–274, 606/278
See application file for complete search history.

(56) References Cited

U.S. PATENT DOCUMENTS

| | | |
|---|---|---|
| 5,207,678 A | 11/1993 | Harms |
| 5,360,431 A | 11/1994 | Puno |
| 5,443,467 A | 8/1995 | Biedermann |
| 5,476,464 A | 12/1995 | Metz-Stavenhagen |
| 5,496,321 A | 3/1996 | Puno |
| 5,554,157 A | 9/1996 | Errico |
| 5,672,176 A | 9/1997 | Biedermann |
| 5,690,630 A | 11/1997 | Errico |
| 5,733,286 A | 3/1998 | Errico |
| 5,782,833 A | 7/1998 | Haider |
| 5,797,911 A | 8/1998 | Sherman |
| 5,810,819 A | 9/1998 | Errico |
| 5,863,293 A | 1/1999 | Richelsoph |
| 5,879,350 A | 3/1999 | Sherman |
| 5,910,142 A | 6/1999 | Tatar |
| 5,964,760 A | 10/1999 | Richelsoph |
| 5,989,250 A | 11/1999 | Wagner |
| 6,010,503 A | 1/2000 | Richelsoph |
| 6,053,917 A | 4/2000 | Sherman |
| 6,261,287 B1 | 7/2001 | Metz-Stavenhagen |
| 6,355,040 B1 | 3/2002 | Richelsoph |
| 6,540,748 B2 | 4/2003 | Lombardo |
| 6,565,565 B1 | 5/2003 | Yuan |
| 6,740,086 B2 | 5/2004 | Richelsoph |

(Continued)

*Primary Examiner* — Jacqueline T Johanas
(74) *Attorney, Agent, or Firm* — Maginot, Moore & Beck, LLP

(57) ABSTRACT

A fixation system comprises a rod, a fastener including a head and an elongated shank, a yoke and an insert. The yoke includes opposite arms defining a slot to receive the rod, an opening to receive the shank, a surface for supporting the fastener head, and a cross bore through each of the arms. The insert has a base configured for slidable insertion between the yoke arms, and defining a rod supporting surface and an opening sized to receive the fastener shank. The insert further includes a pair of resiliently deflectable fingers extending from the base and including a tab projecting therefrom configured to be received within a cross bore. Each tab defines a beveled face configured to bear against the yoke as the insert is advanced into the yoke slot and to deflect the fingers inward until the tabs are aligned with the cross bores.

18 Claims, 4 Drawing Sheets

(56) References Cited

U.S. PATENT DOCUMENTS

| | | |
|---|---|---|
| 7,261,714 B2 | 8/2007 | Richelsoph |
| 8,100,946 B2 * | 1/2012 | Strausbaugh ...... A61B 17/7032 606/266 |
| 8,221,472 B2 * | 7/2012 | Peterson ............ A61B 17/7032 606/270 |
| 8,663,292 B2 * | 3/2014 | Dec .................... A61B 17/7091 606/279 |
| 2004/0073218 A1 | 4/2004 | Dahners |
| 2004/0267264 A1 * | 12/2004 | Konieczynski et al. ........ 606/73 |
| 2007/0118123 A1 * | 5/2007 | Strausbaugh ...... A61B 17/7032 606/272 |
| 2007/0270813 A1 * | 11/2007 | Garamszegi .................... 606/61 |
| 2008/0161859 A1 * | 7/2008 | Nilsson ......................... 606/266 |
| 2008/0183215 A1 * | 7/2008 | Altarac et al. ................ 606/265 |
| 2008/0243193 A1 * | 10/2008 | Ensign et al. ................. 606/305 |
| 2008/0294202 A1 * | 11/2008 | Peterson ............ A61B 17/7032 606/305 |
| 2009/0105770 A1 * | 4/2009 | Berrevoets et al. .......... 606/308 |
| 2009/0254125 A1 * | 10/2009 | Predick .............. A61B 17/7037 606/264 |
| 2009/0270916 A1 * | 10/2009 | Ramsay et al. ............... 606/246 |
| 2010/0063552 A1 * | 3/2010 | Chin et al. .................... 606/302 |
| 2010/0179602 A1 * | 7/2010 | Dauster et al. ............... 606/308 |
| 2010/0234902 A1 * | 9/2010 | Biedermann ...... A61B 17/7037 606/305 |
| 2011/0046683 A1 * | 2/2011 | Biedermann ...... A61B 17/7035 606/305 |
| 2011/0160779 A1 * | 6/2011 | Schlaepfer et al. .......... 606/305 |

* cited by examiner

POLY-AXIAL IMPLANT FIXATION SYSTEM

CROSS-REFERENCE TO RELATED APPLICATION

This application claims priority to co-pending provisional application Ser. No. 61/261,597, filed on Nov. 16, 2009, and incorporates by reference herein the entire specification of this provisional application.

BACKGROUND

The present invention relates to implant fixation systems, and particularly to systems for engaging an elongated member, such as a spinal rod, to a bone. The invention further pertains to a system utilizing a poly- or multi-axial bone fastener.

In many orthopaedic procedures, an implant is fixed to a bone to stabilize the bone. One example is for stabilization of a spinal segment. In one type of spinal fixation system, an elongated stabilization member, such as a spinal rod, is engaged to adjacent vertebrae by a bone engaging member. The bone engaging member is typically a hook configured to engage certain portions of the vertebral anatomy, or a bone screw adapted to be threaded into vertebral bone.

In orthopaedic stabilization systems, and most particularly in spinal systems, there is a need to accommodate various angular orientations between the elongated member and the spinal segment. This necessarily requires an ability to achieve variable angles between the bone engaging member and the elongated stabilization member. In the simplest case, the variable angle is in a single plane. In more complex cases, multi- or poly-axial angular orientations are required. One form of spinal stabilization system utilizes a bone screw having a generally spherically-shaped head. The screw head is seated within a mating cavity in a yoke. The yoke includes opposite arms forming a U-shaped slot for receipt of a spinal rod above the screw head.

Various mechanisms have been developed to lock the screw head and the rod within the yoke. In one such system, an insert is disposed between the bone screw head and the spinal rod. A set screw threaded into the arms of the yoke presses the rod into the insert, which presses the screw head into the yoke cavity. When fully tightened, the set screw effectively locks all of the components of the stabilization assembly together. The strength or tightness of this fixation requires that all of the components be properly oriented, otherwise no amount of tightening of the set screw will fully lock the assembly together. Since the components of the fixation system are typically assembled in situ, the surgeon's ability to visualize the instrumentation is limited. There is therefore a need for an implant fixation system that can provide assurances to the surgeon that the components are properly situated so that the components can be effectively locked together when the instrumentation is complete.

SUMMARY

In one aspect, a fixation system is provided comprising an elongated rod, a fastener including a head and an elongated shank having a bone engaging portion, a yoke and an insert. The yoke includes opposite arms defining a slot therebetween sized for receiving the rod therein, a base portion defining an opening in communication with the slot sized to receive the shank of the fastener therethrough and a surface adjacent the opening for supporting the head of the fastener. In one feature, the yoke further defines a cross bore through each of the arms.

The insert includes a base configured for slidable insertion between the arms of the yoke, the base defining a rod supporting surface configured to support the rod thereon and an opening sized to receive the shank of the fastener therethrough. In a further feature, the insert includes a pair of resiliently deflectable fingers extending from the base to define a slot configured to receive the rod therebetween. Each of the resiliently deflectable fingers include a tab projecting outwardly therefrom and configured to be received within a cross bore in a corresponding one of the arms of the yoke. Each tab defines a beveled face configured to bear against the opposite arms of the yoke as the insert is advanced into the slot of the yoke to deflect the resiliently deflectable fingers toward each other until the insert is advanced far enough into the yoke for the tabs to align with the cross bores in the arms of the yoke. Once the tabs are aligned with the cross bores, the resiliently deflectable arms deflect outward to their natural configuration so that the tabs engage the cross bores.

In a further aspect, each of the tabs may include a flat upper surface configured to prevent removal of the tab from within a corresponding cross bore by translation away from the base portion of the yoke.

The resiliently deflectable fingers and tabs provide a tactile feel and an audible indication when the insert is fully disposed within the yoke. The fingers are further configured to engage the rod within the insert and yoke to form a stable fixation assembly.

DESCRIPTION OF THE FIGURES

FIG. 2 is a cut-away view of the fixation system shown in FIG. 1a.

DETAILED DESCRIPTION

Figure 1A:
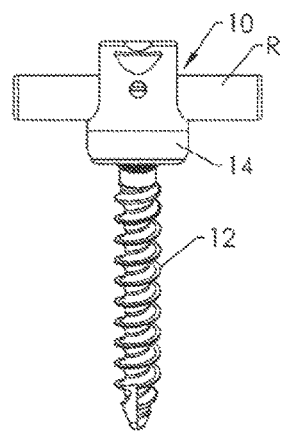
FIGS. 1a-1d are front, rear, side and top views of a poly-axial fixation system according to one embodiment.
Figure 1B:
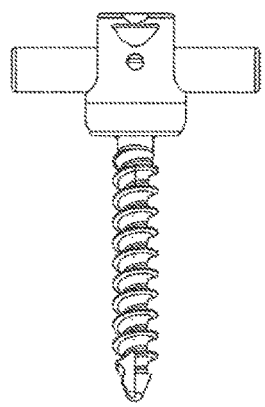
Figure 1C:
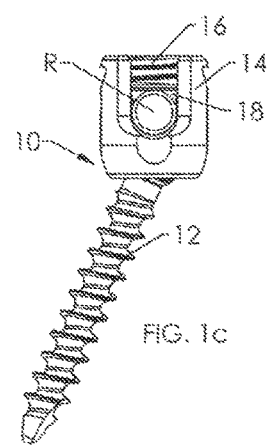
Figure 1D:
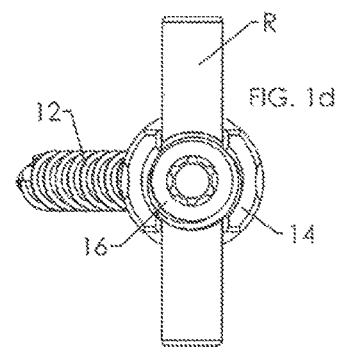

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

An implant fixation assembly 10 shown in FIGS. 1*a-d*, 2 and 3 is adapted for use in spinal fixation and stabilization. The assembly includes a bone engaging fastener 12, in the form of a bone screw and a yoke 14 that couples the bone screw 12 to an elongated stabilization member in the form of a spinal rod R. A set screw 16 is provided that clamps the components together with the bone screw 12 in any one of a plurality of spherical angles relative to the yoke 14. An insert 18 is disposed between the rod R and the bone screw.

Figure 4:
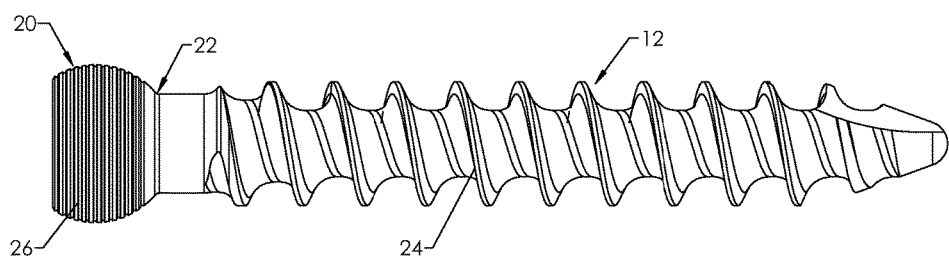
FIG. 4 is a side view of the bone engaging fastener component of the fixation system shown in the prior figures.

As shown in FIG. 4, the bone engaging fastener 12 includes a generally spherically shaped head 20 that blends into a smooth shank 22. The shank of the fastener is provided with bone engaging threads 24 configured for engagement within vertebral bone. The head 20 may be provided with a fixation feature 26 to enhance the fixation between the fastener and the yoke. For example, the fixation feature 26 may include knurling, a roughened surface, or a pattern of grooves that can engage an inner surface of the yoke 14 when the assembly is tightened. The head 20 of the fastener 12 may be provided with an internal feature, such as an internal hex or Torx™ configuration, for mating with a tool to drive the fastener into bone.

Figure 5:
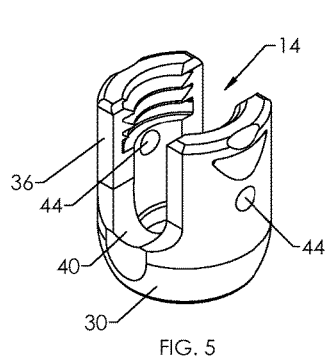
FIG. 5 is a perspective view of the yoke component of the fixation system shown in the prior figures.
Figure 6:
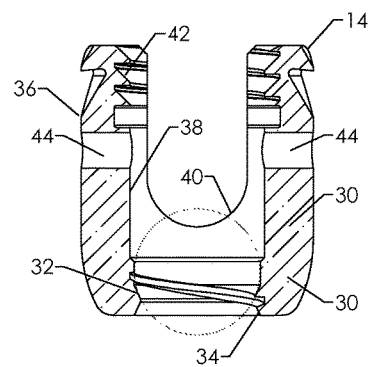
FIG. 6 is a side cross-sectional view of the yoke component shown in FIG. 4.
Figure 7:
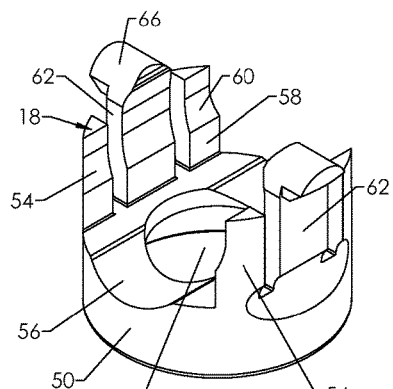
FIG. 7 is a perspective view of the insert component of the fixation system shown in the prior figures.

The yoke component 14 is shown in detail in FIGS. 5-6. The yoke 14 includes a base portion 30 that defines a cavity 32 for receiving and supporting the head 20 of the bone fastener and a bore 34 through which the shank 22 of the fastener passes. The cavity 32 and bore 34 may be configured to permit the bone fastener to move through a range of spherical angles relative to the yoke 14. However, it is contemplated that the yoke and bone screw may be configured for limited movement relative to each other, such as in a single plane, or configured for no relative movement at all.

The yoke includes a pair of opposite arms 36 that define a central bore 38 in communication with the cavity 32. The arms further define a U-shaped slot 40 configured to receive the spinal rod R therein, as shown in FIGS. 1*a-d*. The upper end of the arms 36 may include internal threads 42 configured for threaded engagement with a set screw 16 that is used to clamp the rod R within the yoke. It is, however, contemplated that other structures may be used to fix the rod within the yoke in lieu of the set screw. The yoke further defines a cross bore 44 passing through each arm 36. The cross bore cooperates with the insert 18 as described herein to provide the surgeon with a sensible indicator that the components are properly oriented when assembled in situ. The cross bore 44 may be further configured for engagement by an insertion tool that grasps the yoke to facilitate introduction of the yoke and/or bone screw.

The insert 18 as shown in FIGS. 7-10 includes a base 50 that defines a generally spherical cavity 52 at the underside of the base. The cavity 52 is configured to receive the head 20 of the bone fastener so that the fastener head is contained within an upper and lower cavity formed by cooperation between the insert 18 and yoke 14. The spherical features of the yoke, insert and bone screw accommodate multi-axial movement of the bone screw relative to the yoke. As indicated above, the interface between these components may be configured to limit relative movement accordingly.

Figure 3:
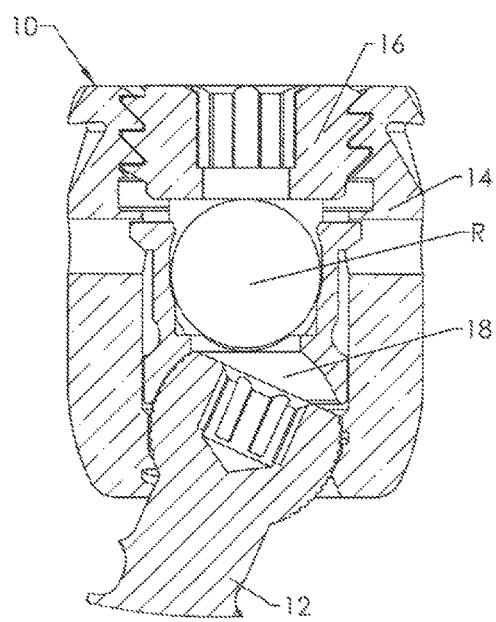
FIG. 3 is an enlarged view of the components of the fixation system shown in FIG. 2.
Figure 2:
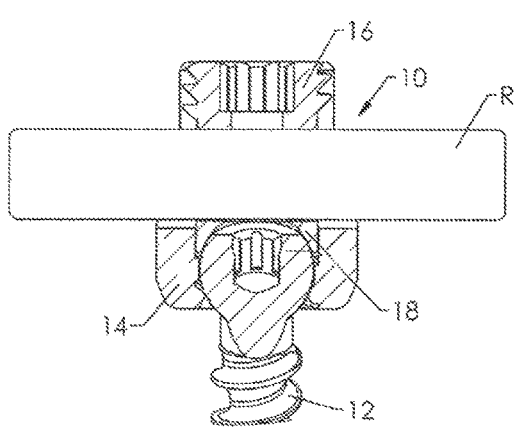

The outer diameter of the base 50 of the insert is sized to pass snugly through the central bore 38 in the yoke, as shown in FIG. 3. In the illustrated embodiment, the base and central bore are generally cylindrical. However, the components may taper in a conical fashion or assume other complementary configurations that permit sliding movement of the insert 18 along the bore 38. The base defines an opening 51 sized to receive the shank 22 of the bone screw 12 therethrough.

Figure 8:
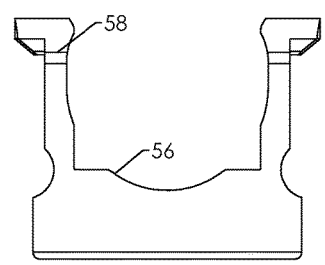
FIG. 8 is a side view of the insert component shown in FIG. 7.
Figure 9:
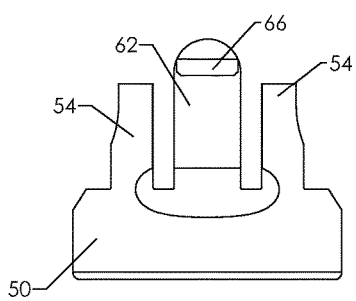
FIG. 9 is an end view of the insert component shown in FIG. 7.
Figure 10:
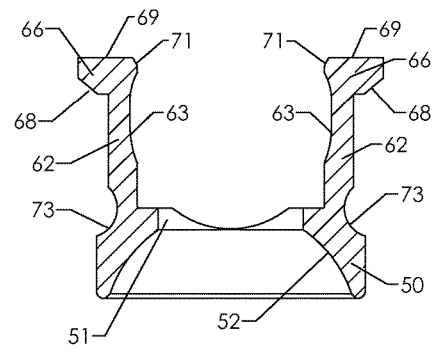
FIG. 10 is a side cross-sectional view of the insert component shown in FIG. 7.
Figure 11:
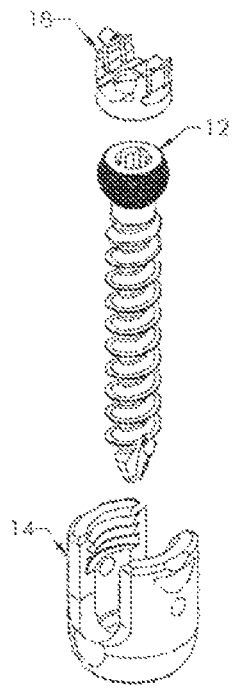
FIG. 11 is an exploded view of the yoke, fastener and insert components shown in the prior figures.

The insert 18 includes opposite side walls 54 that together with the base define a channel 56 and a slot 58, as best seen in FIGS. 8 and 10. The channel 56 may be generally cylindrical to define a rod supporting surface within which the rod is seated. The slot 58 may define a generally curved interior surface 60 to bear against the rod R when the rod is seated within the channel 56 and the insert 18 is disposed within the yoke 14. The interface between the rod R and the curved surface 60 may incorporate features to enhance engagement of the rod within the insert, such as knurling, roughening or other fixation patterns on either the rod, the curved surface or both.

The insert further includes resiliently deflectable fingers 62 situated between or flanked by the side walls 54. The fingers are attached to the base 50 so that the fingers may deflect relative to the base and to the side walls 54. In one embodiment, the base defines an undercut 71 at the connection of the fingers 62 to the base 50. The undercut 71 acts as a resilient hinge to permit flexing of the fingers relative to the base 50. Alternatively, the resiliently deflectable fingers 62 may be configured to bend along their length.

The resiliently deflectable fingers include a generally curved inner surface 63 that may be at least initially contiguous with the interior surface 60 of the side walls. The inner surface 63 is configured to engage or substantially conform to the sides of the spinal rod R when it is disposed within the insert and seated on the rod supporting surface of the base 50. The rod is thus engaged at three locations—at the bottom of the rod by the curved surface 56 and at its sides by the surface 63 of the two resiliently deflectable fingers 62. The resiliently deflectable fingers 62 include outwardly projecting tabs 66 that may incorporate a beveled lower face 68 as shown in FIG. 10. The tabs 66 extend to an outer diameter that is greater than the outer diameter of the base 50 and greater than the inner diameter of the central bore 38 of the yoke 18.

The tabs 66 may be provided with inwardly projecting portions 71 that project slightly inward across the channel formed by the side walls 54. The portions 71 are spaced apart a distance that is slightly less than the diameter of the spinal rod R. These portions 71 provides some resistance to the insertion of a spinal rod between the resiliently deflectable fingers of the insert. Thus, as the rod is introduced into the insert, the fingers 62 deflect outward slightly as the rod passes between the inwardly projecting portions 71. Once the rod is seated against the curved surface 56, the fingers return to the undeflected position shown in FIG. 10 with the portions 71 slightly encircling the rod. This configuration helps retain the rod within the insert 18 as it is introduced into the yoke 14.

The components are assembled as shown in FIGS. 2, 3, 11 and 12. The bone fastener 12 is passed through the bore 34 in the yoke 14 and is driven into the bone a predetermined depth. The yoke is thus initially anchored to the bone, although the fastener head is not yet fixed within the cavity 32, so that the yoke 14 is free to articulate or angulate relative to the fastener and bone.

The spinal rod R is placed within the channel 56 of the insert 18 and the insert is then pushed into the central bore 38 of the yoke 14 with the rod R aligned with the U-shaped slot 40 of the yoke. As the insert passes into the central bore, the beveled face 68 of the tab 66 on each resiliently deflectable finger 62 contacts the top of the yoke. As the insert is pushed farther into the central bore, the beveled face of the tabs forces the resiliently deflectable fingers 62 to deflect inward to fully engage the sides of the rod R.

Figure 12:
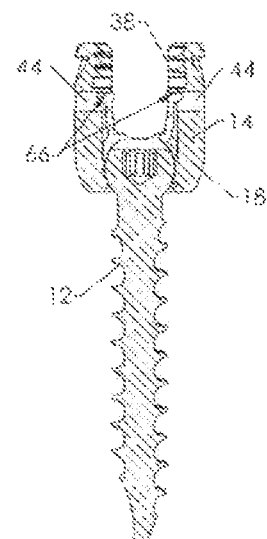
FIG. 12 is a side cross-sectional view of the yoke, fastener and insert components in their assembled configuration.

The insert is pushed deeper into the yoke until the tabs 66 reach the cross bores 44 in the yoke arms 36, at which point the resilience of the fingers 62 causes the tabs to deflect outward into the cross bores, as shown in FIG. 12. This action between the resiliently deflectable fingers and the yoke cross bores provides both a tactile and an audible sensory signal that the insert and rod are properly seated within the yoke and over the fastener head. With the insert 18 situated as shown in FIG. 12 the bone screw and rod are provisionally coupled together. The fingers 62 are configured with a flat upper surface 69 (FIG. 10) so that the upper surface engages the top of the cross bores 66 to prevent removal of the insert, or more particularly to restrict retrograde movement of the insert away from the base portion of the yoke The cross bores 44 have sufficient depth so that the tabs 66 can translate downward toward the cavity 32 of the yoke, as seen in FIGS. 3 and 12. Thus, when the set screw 16 is threaded into the internal threads 42 of the yoke, the set screw 16 bears against the rod R seated within the channel 56 of the insert 18. This in turn pushes the insert deeper into the yoke central bore and thereby presses the cavity 52 of the insert into the fastener head 20. The tabs 66 thus translate downward within the cross bores 44 until the beveled face 68 contacts the base of the cross bores. As the set screw is threaded further into the yoke, the beveled face of the tabs tend to push the resiliently deflectable fingers inward to engage the rod more tightly. Moreover, an opposite reaction causes the base portion 30 of the yoke 14 to be pulled upward toward the insert 18. When the set screw 16 is fully tightened, the head 20 of the fastener 12 is thus tightly clamped between the yoke cavity 32 and the insert cavity 52. Moreover, the rod R is tightly clamped between the set screw 16 and the channel 56 of the yoke.

Figure 13:
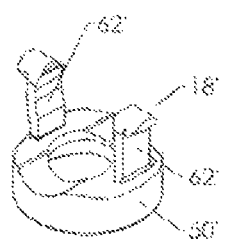
FIGS. 13 and 14 are perspective views of alternative versions of the insert component for a fixation system as disclosed herein.
Figure 14:
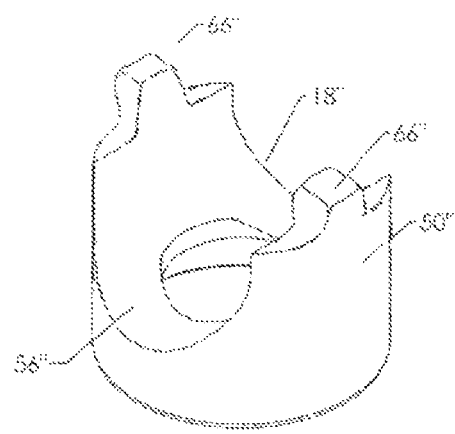

Alternative embodiments of the insert are shown in FIGS. 13 and 14. The insert 18' of FIG. 13 includes resiliently deflectable fingers 62' projecting from the base 50'. In this embodiment, the insert does not include the side walls 54 found in the insert 18 of FIG. 7. Thus, the engagement of the rod is accomplished solely by the resiliently deflectable fingers 62'.

In the embodiment of FIG. 14, the insert 18" includes a base 50" that extends upward and forms a rod engaging surface 56" adapted to receive the spinal rod R. The upper extent of the base 50" defines resiliently deflectable tabs 66" that project outward to engage the cross bores 44 as described above. In this embodiment the insert 18" does not include the resiliently deflectable fingers 62 of the prior embodiment so the insert does not engage the sides of the spinal rod. However, the resiliently deflectable tabs 66" provide the same audible and tactile sensory indication when the insert 18" is properly positioned within the yoke 14.

It is contemplated that the components of the fixation systems described herein are formed of medical grade materials, such as stainless steel and titanium. It is further contemplated that the components may be formed by machining, forging or casting in a conventional manner.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A fixation system comprising:
   an elongated rod having a diameter;
   a fastener including a head and an elongated shank having a bone engaging portion;
   a yoke including opposite arms defining a slot therebetween sized for receiving said rod therein, a base portion defining an opening in communication with said slot sized to receive said shank of said fastener therethrough and a surface adjacent said opening for supporting said head of said fastener, said yoke further defining a cross bore passing through each of said arms transverse to said slot;
   an insert having a base configured for slidable insertion between said arms of said yoke, said base defining a rod supporting surface supporting the rod thereon when said insert is within said yoke, said base further defining an opening for providing access to the head of said fastener therethrough, said insert further including a pair of resiliently deflectable fingers extending from said base to define a slot configured to receive said rod therebetween, each of said resiliently deflectable fingers including a tab projecting therefrom toward said cross bore when said insert is disposed within said yoke and configured to be received within a cross bore in a corresponding one of said arms of said yoke, each tab defining a beveled face configured to bear against said opposite arms of said yoke as said insert is advanced into said slot of said yoke, said beveled face configured to deflect said resiliently deflectable fingers toward each other until said insert is advanced far enough into said yoke for said tabs to align with said cross bores in said arms of said yoke, said insert further including a pair of side walls corresponding to each of said resiliently deflectable fingers, each side wall of said pair of side walls extending from said base and offset from and flanking a corresponding one of said resiliently deflectable fingers, wherein each resiliently deflectable finger is deflected relative to each corresponding side wall of said pair of side walls away from said yoke as the insert is slidably inserted into said yoke,
   wherein said tab of each of said resiliently deflectable fingers includes an inwardly projecting portion projecting into said slot of said insert and spaced apart a distance less than the diameter of said elongated rod.

2. The fixation system of claim 1, wherein each of said tabs includes a flat upper surface configured to prevent removal of said tab from within a corresponding cross bore by translation away from said base portion of said yoke.

3. The fixation system of claim 1, wherein each of said resiliently deflectable fingers defines a curved interior surface extending along substantially the entire length of the fingers configured to substantially conform to the surface of said elongated rod when said rod is seated on said rod supporting surface.

4. The fixation system of claim 1, wherein each of said resiliently deflectable fingers is connected to said base of said insert by a resilient hinge.

5. The fixation system of claim 4, wherein said resilient hinge is an undercut between said base and each of said resiliently deflectable fingers.

6. The fixation system of claim 1, wherein each of said resiliently deflectable fingers is configured to bend along a length thereof.

7. The fixation system of claim 1, wherein said base of said insert defines a surface opposite said rod supporting surface configured to contact said head of said fastener.

8. The fixation system of claim 7, wherein:
said head of said fastener is substantially spherical; and
said opposite surface is substantially spherical.

9. The fixation system of claim 1, wherein said inwardly projecting portion is spaced from said rod supporting surface a distance greater than half the diameter of the rod supported on said rod supporting surface.

10. An assembly for fixing an elongated rod to a fastener including a head and an elongated shank having a bone engaging portion, said assembly comprising:
a yoke including opposite arms defining a slot therebetween sized for receiving the rod therein, a base portion defining an opening in communication with said slot sized to receive the shank of the fastener therethrough and a surface adjacent said opening for supporting the head of the fastener, said yoke further defining a cross bore passing through each of said arms transverse to said slot;
an insert having a base configured for slidable insertion between said arms of said yoke, said base defining a rod supporting surface supporting the rod thereon when said insert is within said yoke, said base further defining an opening for providing access to the head of the fastener therethrough, said insert further including a pair of resiliently deflectable fingers extending from said base to define a slot configured to receive the rod therebetween, each of said resiliently deflectable fingers including a tab projecting therefrom and configured to be received within a cross bore in a corresponding one of said arms of said yoke, each tab defining a beveled face configured to bear against said opposite arms of said yoke as said insert is advanced into said slot of said yoke, said beveled face configured to deflect said resiliently deflectable fingers toward each other until said insert is advanced far enough into said yoke for said tabs to align with said cross bores in said arms of said yoke, said insert further including a pair of side walls corresponding to each of said resiliently deflectable fingers, each side wall of said pair of side walls extending from said base and offset from and flanking a corresponding one of said resiliently deflectable fingers, wherein each resiliently deflectable finger is deflected relative to each corresponding side wall of said pair of side walls as the insert is slidably inserted into said yoke,
wherein said tab of each of said resiliently deflectable fingers includes an inwardly projecting portion projecting into said slot of said insert and spaced apart a distance less than a diameter of the elongated rod.

11. The assembly of claim 10, wherein each of said tabs includes a flat upper surface configured to prevent removal of said tab from within a corresponding cross bore by translation away from said base portion of said yoke.

12. The assembly of claim 10, wherein each of said resiliently deflectable fingers defines a curved interior surface extending along substantially the entire length of the fingers configured to substantially conform to the surface of the elongated rod when the rod is seated on said rod supporting surface.

13. The assembly of claim 10, wherein each of said resiliently deflectable fingers is connected to said base of said insert by a resilient hinge.

14. The assembly of claim 13, wherein said resilient hinge is an undercut between said base and each of said resiliently deflectable fingers.

15. The assembly of claim 10, wherein each of said resiliently deflectable fingers is configured to bend along a length thereof.

16. The assembly of claim 10, wherein said base of said insert defines a surface opposite said rod supporting surface configured to contact said head of said fastener.

17. The assembly of claim 16, wherein:
said head of said fastener is substantially spherical; and
said opposite surface is substantially spherical.

18. The assembly of claim 10, wherein said inwardly projecting portion is spaced from said rod supporting surface a distance greater than half the diameter of the rod supported on said rod supporting surface.

* * * * *